(12) United States Patent
Kane et al.

(10) Patent No.: US 11,273,037 B2
(45) Date of Patent: Mar. 15, 2022

(54) CONDUCTANCE MODE DEPLOYMENT SENSORS FOR TRANSCATHETER VALVE SYSTEM

(71) Applicant: BOSTON SCIENTIFIC SCIMED, INC., Maple Grove, MN (US)

(72) Inventors: Michael J. Kane, Saint Paul, MN (US); Daniel J. Foster, Lino Lakes, MN (US); Stephen J. Burke, Clonmel (IE); Kevin Robert Poppe, New Brighton, MN (US); Peter James Keogh, Dublin (IE); Christopher Jay Scheff, Elk River, MN (US); Bradley S. Swehla, Eagan, MN (US); Laura Kathryn Irvine, Woodbury, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 404 days.

(21) Appl. No.: 16/253,021

(22) Filed: Jan. 21, 2019

(65) Prior Publication Data

US 2019/0224010 A1 Jul. 25, 2019

Related U.S. Application Data

(60) Provisional application No. 62/619,371, filed on Jan. 19, 2018.

(51) Int. Cl.
*A61F 2/24* (2006.01)
*A61F 2/95* (2013.01)
(Continued)

(52) U.S. Cl.
CPC ............ *A61F 2/2436* (2013.01); *A61B 5/063* (2013.01); *A61B 5/6852* (2013.01);
(Continued)

(58) Field of Classification Search
None
See application file for complete search history.

(56) References Cited

U.S. PATENT DOCUMENTS 5,665,103 A * 9/1997 Lafontaine ............... A61B 5/05
606/192
8,579,962 B2 11/2013 Salahieh et al.
(Continued)

FOREIGN PATENT DOCUMENTS

WO 2013074662 A1 5/2013
WO 2016100806 A1 6/2016

OTHER PUBLICATIONS

International Search Report and Written Opinion dated Mar. 25, 2019 for International Application No. PCT/US2019/014407.

*Primary Examiner* — Shaun L David
(74) *Attorney, Agent, or Firm* — Seager, Tufte & Wickhem LLP

(57) ABSTRACT

A delivery system for an implantable medical device includes an outer shaft and an inner shaft translatable within the outer shaft. An internally exposed coil is disposed within the inner shaft and is electrically coupled to an externally exposed coil that can be used to inductively transmit a current flowing through the internally exposed coil. An actuation member extends within the inner shaft and includes a coupler, a force translation rod that extends proximally from the coupler and a plurality of push pull rods that extend distally from the coupler and that releasably couple to the implantable medical device. As the force translation rod moves relative to the internally exposed coil, an impedance varies in accordance with relative position.

9 Claims, 14 Drawing Sheets

(51) Int. Cl.
*A61B 5/06* (2006.01)
*A61B 5/00* (2006.01)
*A61B 90/00* (2016.01)

(52) U.S. Cl.
CPC ..... *A61F 2/2439* (2013.01); *A61B 2090/0811* (2016.02); *A61F 2002/9511* (2013.01)

(56) References Cited

U.S. PATENT DOCUMENTS

| | | |
|---|---|---|
| 2007/0265637 A1 | 11/2007 | Andreas et al. |
| 2008/0188921 A1 | 8/2008 | Yamasaki et al. |
| 2010/0198346 A1 | 8/2010 | Keogh et al. |
| 2010/0318173 A1* | 12/2010 | Kolandaivelu ............ A61F 2/86 623/1.11 |
| 2011/0046713 A1* | 2/2011 | Cully ......................... A61F 2/95 623/1.13 |
| 2011/0306867 A1* | 12/2011 | Gopinathan ............ A61B 5/064 600/407 |
| 2014/0296974 A1* | 10/2014 | Meyer-Brodnitz ... A61F 2/2433 623/2.11 |
| 2015/0148601 A1* | 5/2015 | Weiner .................... A61B 1/012 600/109 |
| 2016/0354160 A1* | 12/2016 | Crowley ............. A61B 1/2676 |
| 2016/0367638 A1 | 12/2016 | Byers et al. |
| 2017/0020669 A1 | 1/2017 | Bartels et al. |
| 2019/0025040 A1* | 1/2019 | Andreason ............. A61B 34/20 |

* cited by examiner

CONDUCTANCE MODE DEPLOYMENT SENSORS FOR TRANSCATHETER VALVE SYSTEM

CROSS-REFERENCE TO RELATED APPLICATIONS

This application claims the benefit of priority under 35 U.S.C. § 119 to U.S. Provisional Application Ser. No. 62/619,371, filed Jan. 19, 2018, the entirety of which is incorporated herein by reference.

TECHNICAL FIELD

The present disclosure pertains to medical devices, and methods for manufacturing medical devices. More particularly, the present disclosure pertains to medical delivery devices with position detection.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example of the disclosure is a delivery system for an implantable medical device. The delivery system includes an outer shaft defining an outer shaft lumen and an inner shaft that is translatable within the outer shaft lumen and that defines a lumen extending through the inner shaft. An internally exposed coil is disposed within the inner shaft and is electrically coupled to an externally exposed coil that can be used to conductively transmit a current flowing through the internally exposed coil. An actuation mechanism extends through the lumen and includes a coupler, a force translation rod that extends proximally from the coupler and a plurality of push pull rods that extend distally from the coupler and that releasably couple to the implantable medical device. The force translation rod is formed of an electrically conducting material with an electrically insulating outer layer, with one or more etched areas extending through the electrically insulating outer layer, wherein when the force translation rod moves relative to the inner shaft, and thus the one or more etched areas move relative to the internally exposed coil, an impedance varies in accordance with relative position.

Alternatively or additionally to any embodiment above, the delivery system may further include a detection region formed in the inner shaft and disposed relative to the internally exposed coil.

Alternatively or additionally to any embodiment above, the delivery system may further include a front seal disposed at a front edge of the detection region and a rear seal disposed at a rear edge of the detection region.

Alternatively or additionally to any embodiment above, the front seal and/or the back seal may include an O-ring.

Alternatively or additionally to any embodiment above, the force translation rod may include an etched or otherwise exposed proximal end so that electrical contact can be made with the force translation rod.

Alternatively or additionally to any embodiment above, the electrically insulating outer layer on the force translation rod may include a polymer.

Alternatively or additionally to any embodiment above, the electrically insulating outer layer on the force translation rod may include Parylene or expanded polytetrafluoroethylene.

Alternatively or additionally to any embodiment above, each of the one or more etched areas may be electrically conductive.

Alternatively or additionally to any embodiment above, each of the one or more etched areas may be located a known distance from the coupler.

Another example of the disclosure is a delivery system for an implantable medical device. The delivery system includes an outer shaft defining an outer shaft lumen and an inner shaft that is translatable within the outer shaft lumen. The inner shaft defines a lumen extending through the inner shaft. An actuation mechanism extends through the lumen and includes a coupler, a force translation rod that extends proximally from the coupler and a plurality of push pull rods that extend distally from the coupler and that releasably couple to the implantable medical device. The force translation rod is formed of or including an electrically conducting material with an electrically insulating outer layer, with one or more electrically conductive etched areas extending through the electrically insulating outer layer. A resilient switch is coupled to the inner shaft and is positioned to slidingly engage the force translation rod such that as the force translation rod translates, the resilient switch comes into contact with the one or more electrically conductive etched areas. When the force translation rod moves relative to the inner shaft, and thus the one or more etched areas move relative to the internally exposed coil, an impedance varies in accordance with relative position.

Alternatively or additionally to any embodiment above, the force translation rod may include an etched or selectively electrically active proximal end so that electrical contact can be made with the force translation rod.

Alternatively or additionally to any embodiment above, the electrically insulating outer layer on the force translation rod may include a polymer.

Alternatively or additionally to any embodiment above, the electrically insulating outer layer on the force translation rod may include Parylene or expanded polytetrafluoroethylene.

Alternatively or additionally to any embodiment above, each of the one or more etched areas may be located a known distance from the coupler.

Alternatively or additionally to any embodiment above, the inner shaft may include an outer surface, and the outer surface may include one or more longitudinally extending slots that accommodate electrical conductors within the one or more longitudinally extending slots.

Alternatively or additionally to any embodiment above, the one or more electrically conducting etched areas may include a plurality of etched bars extending radially at least partially around the force translation rod.

Alternatively or additionally to any embodiment above, the plurality of etched bars extending radially at least partially around the force translation rod may be arranged with a non-uniform axial spacing between adjacent etched bars.

Another example of the disclosure is a delivery system for an implantable medical device. The delivery system includes an outer shaft defining an outer shaft lumen and an inner shaft that is translatable within the outer shaft lumen and that itself defines a lumen extending through the inner shaft. An actuation mechanism extends through the lumen and includes a coupler, a force translation rod that extends proximally from the coupler and a plurality of push pull rods that extend distally from the coupler and that releasably couple to the implantable medical device. The force translation rod includes one or more ferromagnetic segments disposed along a length of the force translation rod. An electromagnetic detector is coupled to the inner shaft and is positioned to slidingly engage the force translation rod such that as the force translation rod translates, the electromagnetic detector comes into proximity with the one or more ferromagnetic segments disposed along the length of the force translation rod.

Alternatively or additionally to any embodiment above, the inner shaft may define an outer surface, and the outer surface may include one or more longitudinally extending slots, and the electromagnetic switch is disposed within one of the one or more longitudinally extending slots.

Alternatively or additionally to any embodiment above, each of the one or more ferromagnetic segments may be located a known distance from the coupler.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
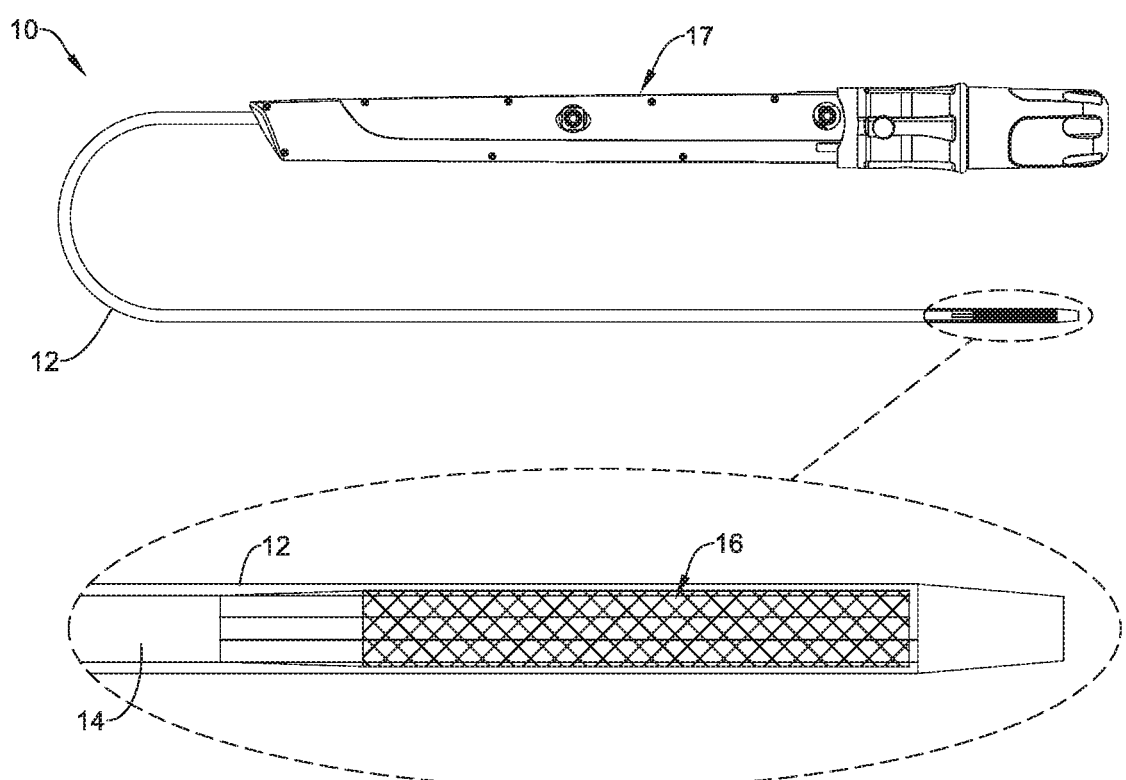
FIG. 1 is a side view of an example medical device system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Diseases and/or medical conditions that impact the cardiovascular system are prevalent throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve or the mitral valve can have a serious effect on a human and could lead to serious health condition and/or death if not dealt with properly. Treatment of defective heart valves poses other challenges in that the treatment often requires the repair or outright replacement of the defective valve. Such therapies may be highly invasive to the patient. Disclosed herein are medical devices that may be used for delivering a medical device to a portion of the cardiovascular system in order to diagnose, treat, and/or repair the system. At least some of the medical devices disclosed herein may be used to deliver and implant a replacement heart valve (e.g., a replacement aortic valve, replacement mitral valve, etc.). In addition, the devices disclosed herein may deliver the replacement heart valve percutaneously and, thus, may be much less invasive to the patient. The devices disclosed herein may also provide a number of additional desirable features and benefits as described in more detail below.

The figures illustrate selected components and/or arrangements of a medical device system 10, shown schematically in FIG. 1 for example. It should be noted that in any given figure, some features of the medical device system 10 may not be shown, or may be shown schematically, for simplicity. Additional details regarding some of the components of the medical device system 10 may be illustrated in other figures in greater detail. A medical device system 10 may be used to deliver and/or deploy a variety of medical devices to a number of locations within the anatomy. In at least some embodiments, the medical device system 10 may include a replacement heart valve delivery system (e.g., a replacement aortic valve delivery system) that can be used for percutaneous delivery of a medical implant 16, such as a replacement/prosthetic heart valve. This, however, is not intended to be limiting as the medical device system 10 may also be used for other interventions including valve repair, valvuloplasty, delivery of an implantable medical device (e.g., such as a stent, graft, etc.), and the like, or other similar interventions.

The medical device system 10 may generally be described as a catheter system that includes an outer sheath 12, an inner catheter 14 (a portion of which is shown in FIG. 1 in phantom line) extending at least partially through a lumen of the outer sheath 12, and a medical implant 16 (e.g., a replacement heart valve implant) which may be coupled to the inner catheter 14 and disposed within a lumen of the outer sheath 12 during delivery of the medical implant 16. In some embodiments, a medical device handle 17 may be disposed at a proximal end of the outer sheath 12 and/or the inner catheter 14 and may include one or more actuation mechanisms associated therewith. In other words, a tubular member (e.g., the outer sheath 12, the inner catheter 14, etc.) may extend distally from the medical device handle 17. In general, the medical device handle 17 may be designed to manipulate the position of the outer sheath 12 relative to the inner catheter 14 and/or aid in the deployment of the medical implant 16.

In use, the medical device system 10 may be advanced percutaneously through the vasculature to a position adjacent to an area of interest and/or a treatment location. For example, in some embodiments, the medical device system 10 may be advanced through the vasculature to a position adjacent to a defective native valve (e.g., aortic valve, mitral valve, etc.). Alternative approaches to treat a defective aortic valve and/or other heart valve(s) are also contemplated with the medical device system 10. During delivery, the medical implant 16 may be generally disposed in an elongated and low profile "delivery" configuration within the lumen and/or a distal end of the outer sheath 12, as seen schematically in FIG. 1 for example. Once positioned, the outer sheath 12 may be retracted relative to the medical implant 16 and/or the inner catheter 14 to expose the medical implant 16. In some instances, the medical implant 16 may be self-expanding such that exposure of the medical implant 16 may deploy the medical implant 16. Alternatively, the medical implant 16 may be expanded/deployed using the medical device handle 17 in order to translate the medical implant 16 into a generally shortened and larger profile "deployed" configuration suitable for implantation within the anatomy. For example, in some instances the inner catheter (or components thereof) may be coupled to medical implant 16 whereby actuation of the inner catheter 14 relative to the outer sheath 12 and/or the medical implant 16 may deploy the medical device 16 within the anatomy. When the medical implant 16 is suitably deployed within the anatomy, the medical device system 10 may be disconnected, detached, and/or released from the medical implant 16 and the medical device system 10 can be removed from the vasculature, leaving the medical implant 16 in place in a "released" configuration.

It can be appreciated that during delivery and/or deployment of an implantable medical device (e.g., the medical implant 16), portions of the medical device system 10 may be required to be advanced through tortuous and/or narrow body lumens. Therefore, it may be desirable to utilize components and design medical delivery systems (e.g., such as the medical device system 10 and/or other medical devices) that reduce the profile of portions of the medical device while maintaining sufficient strength (compressive, torsional, etc.) and flexibility of the system as a whole.

Figure 2:
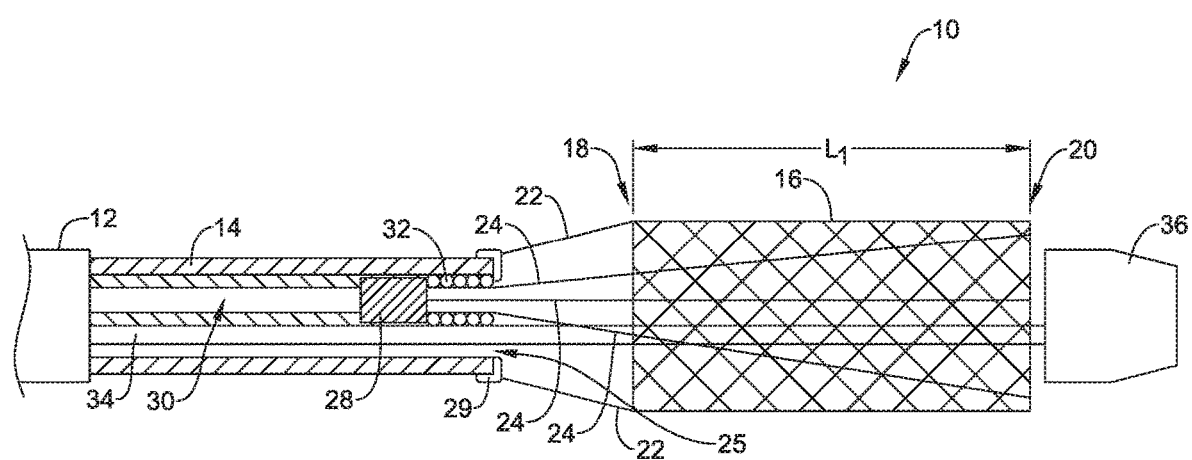
FIG. 2 is a partial cross-sectional view of a portion of an example medical device delivery system.

FIG. 2 illustrates the medical device system 10 in a partially deployed configuration. As illustrated in FIG. 2, the outer sheath 12 of the medical device system 10 has been retracted in a proximal direction to a position proximal of the medical implant 16. In other words, the outer sheath 12 has been retracted (e.g., pulled back) in a proximal direction such that it uncovers the medical device implant 16 from a compact, low-profile delivery position to a partially deployed position.

In at least some examples contemplated herein, the medical device implant 16 may be designed to self-expand once released from under the outer sheath 12. However, as shown in FIG. 2, the medical device system 10 may be designed such that the implant 16 may be restricted from expanding fully in the radial direction. For example, FIG. 2 shows medical device implant 16 having a partially deployed position denoted as a length "$L_1$."

FIG. 2 further illustrates that in some examples, the implant 16 may include one or more support members 22 coupled to the proximal end 18 of the implant 16. Further, FIG. 2 illustrates that in some examples, the implant 16 may include one or more translation members 24 coupled to the distal end 20 of the implant 16. Additionally, in some examples (such as that illustrated in FIG. 2), the translation members 24 and support members 22 may work together to maintain the implant in a partially deployed position after the outer sheath has been retracted to uncover the implant 16. For example, FIG. 2 illustrates that the support members 22 may be designed such that the distal end of each of the support members may be coupled to the proximal end of the implant 16 and that the proximal end of each of the support members 22 may be coupled to the distal end of the inner catheter 14. For example, FIG. 2 illustrates that the proximal ends of the support members 22 may be attached to a containment fitting 28 which is rigidly fixed to the distal end of the inner catheter 14. It can be further appreciated that in some instances, the support members 22 may be designed to limit the proximal movement of the proximal end 18 of the implant 16 relative to the distal end of the inner catheter 14.

Additionally, the translation members 24 may be designed to translate in a distal-to-proximal direction such that the translation of the translation members (via operator manipulation at the handle, for example) may "pull" the distal end 20 of the implant closer to the proximal end 18 of the implant 16.

Figure 3:
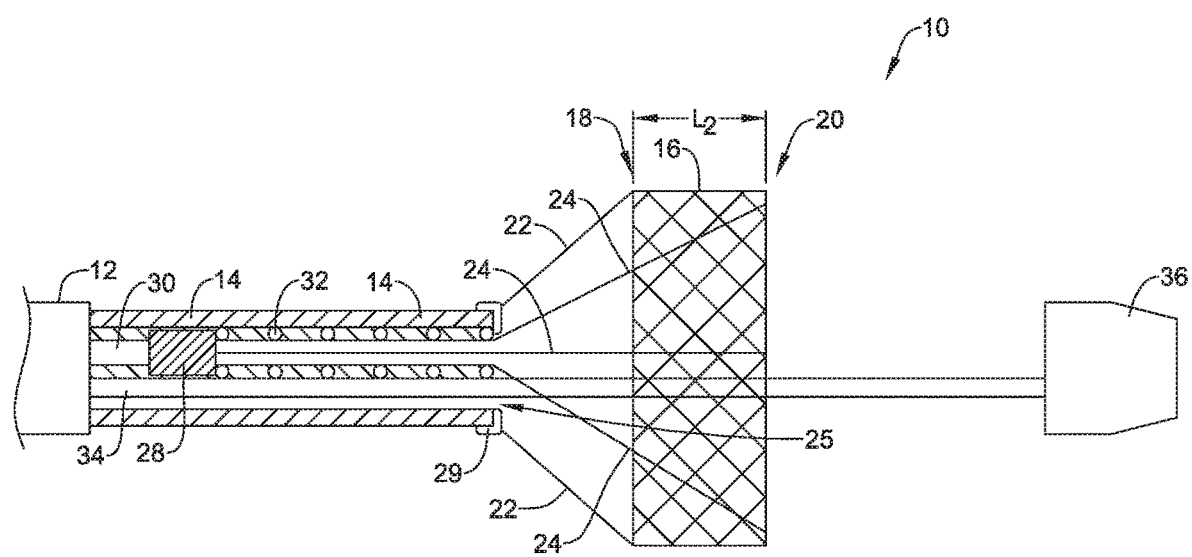
FIG. 3 is a partial cross-sectional view of a portion of an example medical device delivery system.

For example, FIG. 3 illustrates the distal-to-proximal translation of the translation members 24. It can be appreciated that if the support members 22 limit the proximal movement of the proximal end 18 of the implant 16 while the translation members 24 are translated proximally, the implant 16 may both foreshorten (along the longitudinal axis of the implant 16) and also expand radially outward. The foreshortening and radial expansion of implant 16 can be seen by comparing the shape and position of the implant 16 in FIG. 2 to the shape and position of the implant 16 in FIG. 3. The position of the implant 16 shown in FIG. 3 may be described as a fully deployed positioned of the implant 16 (versus the partially deployed positioned of the implant 16 shown in FIG. 2). Further, FIG. 3 depicts the length of the fully deployed implant 16 as $L_2$, whereby the distance $L_2$ is less than the distance $L_1$ shown in FIG. 2.

Additionally, it can be appreciated that the translation members 24 may be designed to be able extend in a proximal-to-distal direction such that they elongate (e.g., lengthen) the implant 16 (along its longitudinal axis). In other words, implant 16 may be able to shift between a partially deployed position (shown in FIG. 2) and a fully deployed position (shown in FIG. 3) through the translation (either proximal or distal) of the translation members 24 along the longitudinal axis as the support members 22 limit the movement of the proximal end 18 of the implant 16.

It should be noted that the above description and illustrations regarding the arrangement, attachment features and operation of the support members 22 and the translation members 24 as they engage and function relative to the implant 16 is schematic. It can be appreciated that the design (e.g., arrangement, attachment features, operation, etc.) of the both support member 22 and the translation members 24 as they relate and function relative to the implant 16 may vary. For example, it is possible to design, arrange and operate the translation members 24 and the support members 22 in a variety of ways to achieve the partial and full deployment configurations of the implant 16.

In some examples, an operator may be able to manipulate the translation members 24 via the handle member 17. For example, the handle 17 may include an actuation member designed to control the translation of the translation members 24. FIG. 2 illustrates that the handle member 17 may be coupled to the translation members 24 via an actuation shaft 30 and a coupling member 28. For example, as will be described in greater detail below, FIG. 2 illustrates that the proximal ends of the translation members 24 may be coupled to a distal end of the coupling member 28. Additionally, FIG. 2 further illustrates that a distal end of actuation shaft 30 may be coupled to the proximal end of the coupling member 28. Further, while not shown in FIG. 2, it can be appreciated that the actuation shaft 30 may extend within the entire length of the inner shaft 14 from the coupling member 28 to the handle member 17.

For purposes of discussion herein, the inner shaft 14 may also be referred to as an inner member or liner 14. The liner 14 may include a number of different features shown in the figures described herein. For example, the liner may include a lumen 25. Further, the translation members 24, coupler 28, actuation shaft 30, guidewire lumen 34 (described below), and grouping coil 32 (described below) may be disposed within the lumen 25. These are just examples. The inner liner 14 may vary in form. For example, the inner liner 14 may include a single lumen, multiple lumens, or lack a lumen.

As described above, FIG. 2 and FIG. 3 illustrate the translation of translation members 24 in a distal-to-proximal direction (which shortens and radially expands the implant 16, as described above). However, FIG. 3 further illustrates that translation of the translation members 24 in a distal-to-proximal direction is accomplished by translation of the actuation shaft 30 and coupling member 28 within the lumen 25 of the inner catheter 14. For example, as the actuation shaft 30 is retracted (e.g., pulled proximally within lumen 25 of the inner catheter 14), it retracts the coupling member 28 proximally, which, in turn, retracts the translation members 24 in a proximal direction.

In some instances it may be desirable to maintain translation members 24 in a substantially linear configuration as they are translated within the lumen 25 of the inner catheter 14. In some examples, therefore, medical device system 10 may include a component designed to limit and/or prevent the translation members 24 from twisting around each other within the lumen 25 of the inner catheter 14. For example, FIG. 2 and FIG. 3 illustrate a grouping coil 32 wound around the translation members 24 such that the grouping coil maintains the translation members 24 in a substantially liner configuration (and thereby limits and/or prevents the translation members 24 from twisting within lumen 25) as the translation members 24 are translated through the lumen 25 of the inner catheter 14.

FIG. 2 and FIG. 3 further illustrate that the proximal end of the grouping coil 32 may be positioned adjacent the distal end of the coupling member 28 and that the distal end of the grouping coil 32 may be positioned adjacent the distal end of the inner catheter 14. In particular, the distal end of the grouping coil 32 may be prevented from extending distally beyond the distal end of the inner catheter 14 by the containment fitting 29. In other words, the distal end of the grouping coil 32 may contact the containment fitting 29.

It can be further appreciated that the grouping coil 32 may be positioned within the lumen 25 of the inner catheter 14 such that the grouping coil 32 may elongate and shorten (e.g., a length of the grouping coil may adjust) within the lumen 25 of the inner catheter 14. For example, as the coupling member 28 is translated in a proximal direction (shown in FIG. 3 as compared to FIG. 2), the grouping coil may elongate while continuing to group and/or contain the translation members 24 in a substantially linear configuration.

FIG. 2 and FIG. 3 further illustrate that the medical device system 10 may include a tubular guidewire member 34 extending within the lumen 25 of the inner catheter 14. The tubular guidewire member 34 may be designed to permit a guidewire to extend and translate therein. Further, the tubular guidewire member 34 may extend from the handle member 17, through the lumen 25 of the inner member 14, through the implant 16 and terminate at a nosecone 36. Additionally the tubular guidewire member 34 may include a lumen (not shown in FIG. 2 or FIG. 3) that permits a guidewire to be advanced therein. In other words, the medical device 10 may be advanced to a target site within a body over a guidewire extending within the lumen of the tubular guidewire member 34.

Figure 4:
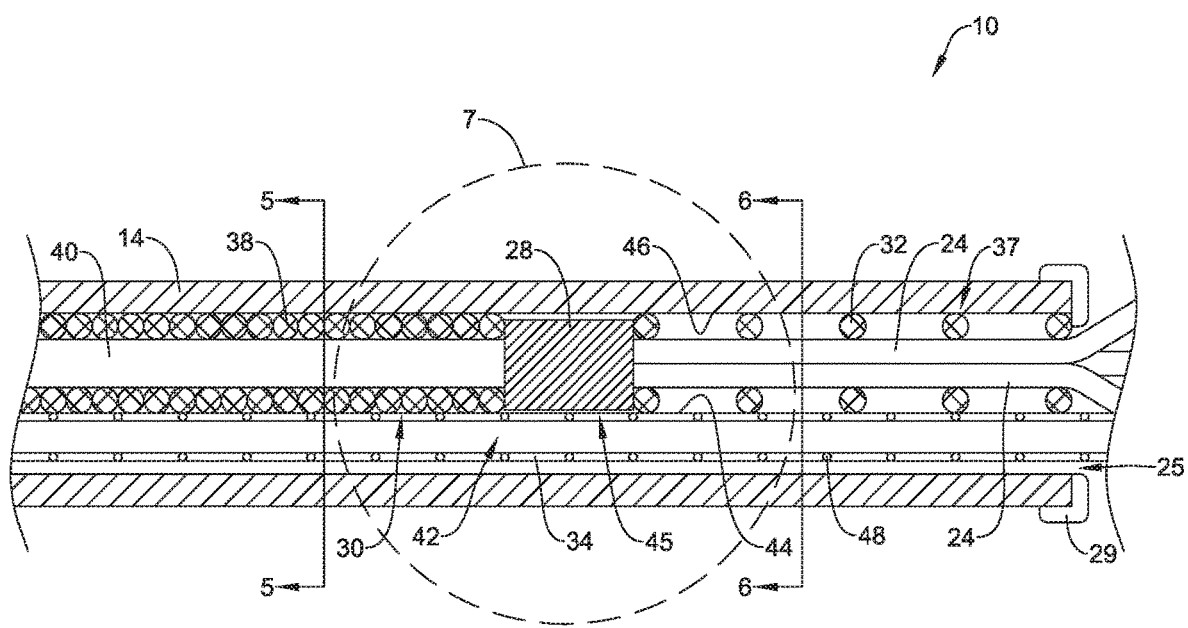
FIG. 4 is a partial cross-sectional view of a portion of the catheter shaft shown in FIGS. 1-3.

FIG. 4 illustrates a cross-section of a portion of the medical device system 10 described with respect to FIGS. 1-3. In particular, as described above, FIG. 4 illustrates the actuation shaft 30 coupled to coupler 28, translation members 24 coupled to coupler 28 and grouping coil 32 (the distal end of which is positioned adjacent the containment fitting 29, as described above) wound around the translation members 24. FIG. 4 further illustrates that the outer surface 37 of the grouping coil 32 may contact both the inner surface 46 of the inner catheter 14 and the outer surface 44 of the guidewire member 34. Therefore, it can be further appreciated that the outer diameter (and therefore the inner diameter) of the grouping coil 32 may remain constant as the grouping coil lengthens or shortens as the coupler 28 translates within the lumen 25 of the inner catheter 14.

Additionally, it can be appreciated that the medical device system 10 may be designed such that both the proximal end and the distal end of the grouping coil 32 may not be fixedly attached to adjacent structures (e.g., may not be attached to the coupling member 28 and/or the containment fitting 29). It can be appreciated that by not attaching either end of the grouping coil 32 to an adjacent structures (e.g., the coupling member 28 and/or the containment fitting 29), the grouping coil 32 is permitted to twist freely while lengthening or shortening within the lumen 25. This freedom of movement allows the grouping coil 32 to maintain an inner diameter which tightly groups (e.g., contains) the translation members 24 to each other as that translate linearly within the lumen 25 of inner catheter 14.

FIG. 4 further illustrates that coupler 28 may be positioned within the lumen 25 of the inner catheter 14 such that the bottom surface 45 of the coupler 28 is adjacent to the outer surface 44 of the guidewire member 34. In some examples, the coupler 28 may be designed such that it is not rigidly fixed to the guidewire member 34, and therefore, may translate relative to the guidewire member 34. In other examples, the coupler 28 may be designed such that it is rigidly fixed to the guidewire member 34, and therefore, translation of coupler 28 (which itself may occur via translation of the actuation shaft 30) may also translate both the guidewire member 34 and the translation members 24. In other words, it can be appreciated that in instances where the coupler 28 is rigidly fixed to the guidewire member 34, an operator manipulating the actuation shaft 30 via handle 17 may translate both the translation members 24 and the guidewire member 34 together such that distal or proximal translation of either the translation members 24 or the guidewire member 34 will translate both the translation members 24 or the guidewire member 34 a correspondingly equal amount. Further, it can be appreciated the same effect may be achieved by coupling the guidewire member 34 and the actuation shaft 30 anywhere along medical device system 10, including coupling the guidewire member 34 and the actuation shaft 30 to one another in the handle member 17. It can be appreciated that the guidewire member 34 and the actuation shaft 30 may be coupled together in more than one location along medical device system 10.

In some instances, it may be desirable for the nosecone 36 to translate in a proximal direction as the implantable medical device 16 shifts from a collapsed configuration to a fully deployed configuration (as shown in FIGS. 1-3). It can be appreciated from the above discussion that because the nosecone 36 is connected to the distal end of the guidewire member 34, that as the guidewire member 34 translates with the translation members 24 (via the coupler 28 and actuation shaft 30), the nosecone 36 with correspondingly translate in a proximal direction as the translational members act to shift the implantable medical device 16 from a collapsed to a fully deployed configuration.

FIG. 4 further illustrates that in some instances actuation shaft 30 may include an actuation rod 40 positioned within the lumen of a coil member 38. Similar to that described above with respect to the grouping coil 32, the outer surface of the coil member 38 may contact both the inner surface 46 of the inner catheter 14 and the outer surface 44 of the guidewire member 34. It can be appreciated that the outer surface of the coil member 38 may reduce the frictional forces of actuation shaft 30 along the inner surface 46 of the inner catheter 14 as compared to the frictional forces that would be present if the actuation shaft 30 did not include a coil member. For example, coil member 38 provides both "point to point" contacts along the inner surface 46 of the inner member 14 in addition to increasing the ease with which the actuation shaft flexes/bends within the lumen 25 of inner catheter 14. These properties reduce the overall surface friction between the outer surface of actuation shaft 30 and the inner surface 46 of inner catheter 14 (as compared to a solid rod of similar proportions). The reduction in friction may further reduce the likelihood of the actuation shaft 30 to store and release energy in the form of a "backlash" effect. It is contemplated that the coil member 38 may be extend along a portion of or the entire length of the actuation rod 40. Further, the actuation rod 40 may extend from the proximal end of the coupler 28 to the handle member 17. Additionally, the above described functional characteristics of the coil member 38 are not intended to be limiting. For example, it is contemplated that the coil member 38 may be utilized to conduct electricity along a portion thereof (e.g., along the surface or other portion of coil member 38).

FIG. 4 further illustrates that in some examples guidewire member 34 may include a reinforcing coil embedded with its tubular wall. For example, FIG. 4 shows coil 48 positioned with the wall of guidewire member 34. Coil 48 may provide additional strength and flexibility to the guidewire member 34. Additionally, FIG. 4 illustrates the lumen 42 of the guidewire member 34. It can be appreciated that a guidewire (not shown) may extend with the lumen 42 of the guidewire member 34.

Figure 5:
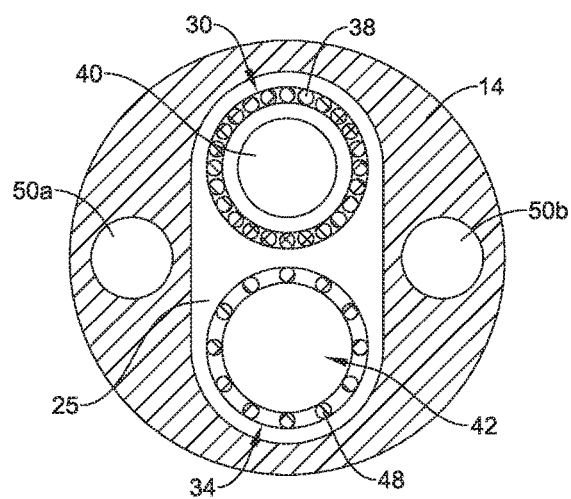
FIG. 5 is a cross-sectional view along line 5-5 of FIG. 4.

FIG. 5 illustrates a cross-sectional view along line 5-5 of FIG. 4. As indicated above, the inner catheter 14 may include a number of features. For example, the inner catheter 14 may include one or more tension resistance members 50a/50b. The tension resistance members 50a/50b may take the form of a wire (e.g., a metallic wire), a braid, cable, stranded cable, a composite structure, or the like. In one example, the tension resistance members 50a/50b are both metallic wires. In another instance, the tension resistance members 50a/50b are both metallic braids. The braids may further includes an axial wire made from a suitable polymer or metal (e.g., aramid). The tension resistance members 50a/50b may be made from the same materials and/or have the same configuration. Alternatively, the tension resistance members 50a/50b may be different from one another. Furthermore, while FIG. 5 illustrates that the inner catheter 14 includes two tension resistance members 50a/50b, this is not intended to be limiting. Other numbers of tension resistance members 50a/50b are contemplated such as one, three, four, five, six, seven, or more.

FIG. 5 further illustrates that the shape of the lumen 25 of the inner catheter 14 may be designed to limit twisting of the actuation shaft 30 and the guidewire member 34. For example, FIG. 5 illustrates that lumen 25 may be non-circular. For example, the shape of the lumen 25 may be ovular, square, rectangular, etc. It can be appreciated that as the inner catheter 14 rotates within the lumen of the outer member 12, the shape of the lumen 25 may force both the actuation shaft 30 and the guidewire member 34 to maintain the respective spatial relationship as depicted in FIG. 5. In other words, the shape of the lumen 25 forces the actuation shaft 30 and the guidewire member 34 to remain in their positions relative to one another independent of the bending, rotating, flexing, etc. of the inner catheter 14.

Additionally, FIG. 5 also illustrates the actuation shaft 30 and the guidewire member positioned adjacent one another within lumen 25. As described above, actuation shaft 30 may include an actuation rod 40 positioned within the lumen of a coil member 38. Additionally, FIG. 5 shows guidewire member 34. The guidewire member 34 may include a reinforcing coil 48 embedded with its tubular wall. For example, FIG. 5 shows coil 48 positioned with the wall of guidewire member 34. Coil 48 may provide additional strength and flexibility to the guidewire member 34. Additionally, FIG. 5 illustrates the lumen 42 of the guidewire member 34.

Figure 6:
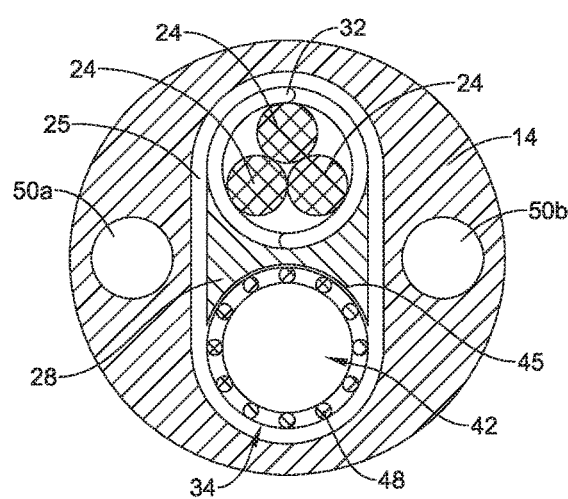
FIG. 6 is a cross-sectional view along line 6-6 of FIG. 4.

FIG. 6 illustrates a cross-sectional view along line 6-6 of FIG. 4. FIG. 4 shows grouping coil 32, coupler 28 and guidewire member 34 positioned within lumen 25. Additionally, FIG. 6 shows that the grouping coil 32 may surround three translational members 24 positioned therein. The translational members 24 may be spaced equidistance from one another. For example, the translational members 24 may be spaced at substantially 120 degree angles relative to one another. Further, while FIG. 6 shows three translational members 24, it is contemplated that more or less than three translational members 24 may be utilized within medical device system 10. For example, medical device system 10 may include 1, 2, 3, 4, 5, 6, 7, 8, 9, 10 or more translational members 24.

Additionally, FIG. 6 illustrates that inner catheter 14 may include one or more tension resistance members 50a/50b. The tension resistance members 50a/50b may take the form of a wire (e.g., a metallic wire), a braid, cable, stranded cable, a composite structure, or the like. Further, FIG. 6 illustrates that tension resistance members 50a/50b may be positioned opposite one another on either side of lumen 25.

Additionally, FIG. 5 shows guidewire member 34. The guidewire member 34 may include a reinforcing coil 48 embedded with its tubular wall. For example, FIG. 5 shows coil 48 positioned with the wall of guidewire member 34. Coil 48 may provide additional strength and flexibility to the guidewire member 34. Additionally, FIG. 5 illustrates the lumen 42 of the guidewire member 34.

FIG. 6 further illustrates the coupler 28 including the bottom surface 45 (described above). As illustrated, the bottom surface 45 is shaped to mate with the outer surface the guidewire member 34. For example, in some examples, the bottom surface 45 may include a curved portion which mates with the radius defined by the outer surface 44 of the guidewire member 34. As described above, the bottom surface 45 of the coupler 28 may or may not be rigidly fixed to the guidewire member 34.

Figure 7:
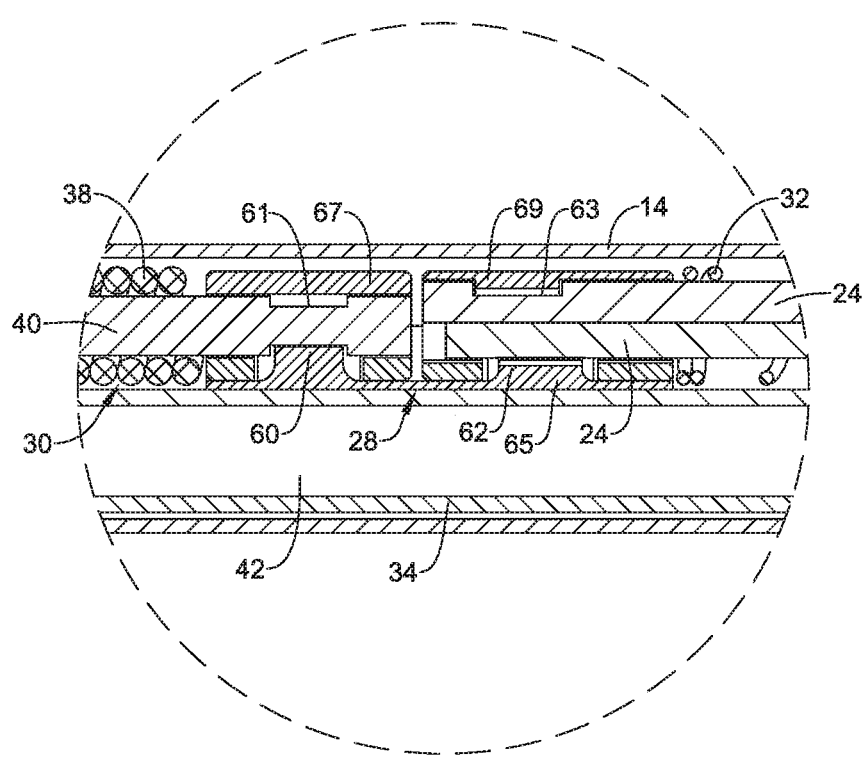
FIG. 7 is a partial cross-sectional view of a portion of an example medical device delivery system.

FIG. 7 illustrates a detailed view of a portion of the medical device system 10 shown in FIG. 6. Further, FIG. 7 illustrates a cross-sectional view of coupler 28. Coupler 28 may include a base member 65, a first cap 67 and a second cap 69. First cap 67 and second cap 69 may be separate components from base member 65. Further, first cap 67 and second cap 69 may be attached to base member 65 via welding or any other suitable process.

As shown, a portion of the actuation rod 40 may extend into a portion of coupler 28 and thereby contact both base member 65 and first cap 67. Similarly, portions of the translational members 24 may extend into a portion of coupler 28 and thereby contact both base member 65 and first cap 69. It can be appreciated from FIG. 7 that base member 65 may include one or more projections 60 that mate with one or more recess 61 in the actuation rod 40. Similarly, it can be appreciated from FIG. 7 that base member 65 may include one or more projections 62 that mate with one or more recesses 63 in the translational members 24. It can further be appreciated that engaging a respective projection with a recess portion (in both the actuation rod 40 and the translational members 24) may limit translational movement of both the actuation rod 40 and the translational members 24 relative to the coupler. In other words, engagement of a respective projection with a recess portion (in both the actuation rod 40 and the translational members 24) may prevent both the actuation rod 40 and the translational members 24 from translating independently of the coupler 28 (and one another). However, it can be further appreciated that the engagement of a respective projection with a recess portion (in both the actuation rod 40 and the translational members 24) may permit the actuation rod 40 to spin/swivel on its own longitudinal axis. Additionally, it can be appreciated that coupler 28 (including base member 65, first cap 67 and second cap 69) may permit dissimilar materials to be engaged because they are mechanically "trapped" and preferentially oriented within coupler 28. In some instances, the coupler 28 may be defined as a "swivel."

Figure 8:
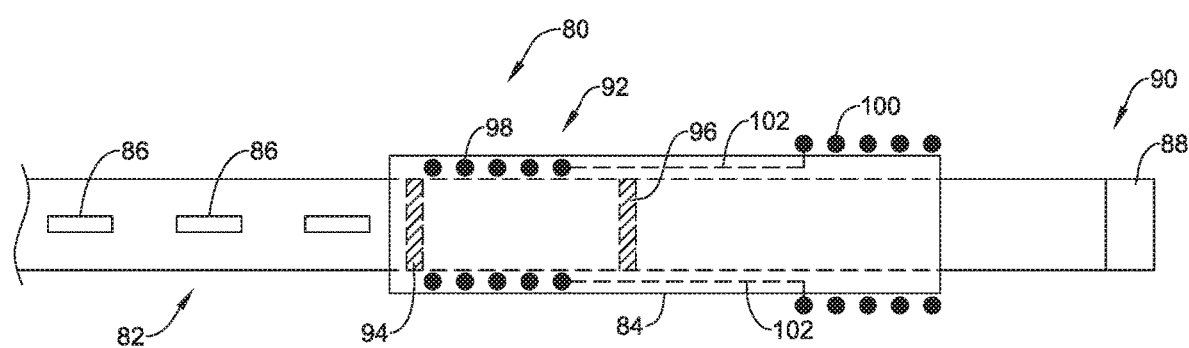
FIG. 8 is a partial view of an example medical device delivery system.

In some cases, it can be beneficial to have an indication of relative position of the actuation rod 40, and thus an indication of the relative position of the coupler 28 and the translational members 24, as this can provide an indication of the relative position of the medical implant 16. FIG. 8 shows a portion of an example medical delivery device 80. It will be appreciated that some features and elements of the medical delivery device 80 may not be illustrated for clarity purposes. The medical delivery device 80 includes an inner rod 82 that is slidingly disposed within an outer sheath 84. In some cases, the inner rod 82 may be considered as representing the actuation rod 40 and the outer sheath 84 may be considered as representing a portion of the inner catheter 14 discussed with respect to previous drawings. In some cases, the outer sheath 84 includes an electrically insulating layer. In some instances, the outer sheath 84 may represent or be a portion of the coil member 38 extending through the lumen 25.

The inner rod 82 may be formed of an electrically conductive material and may be covered with an electrically insulating material. In some cases, the electrically insulating material may be a polymer such as Parylene or expanded polytetrafluoroethyene (better known as Teflon). One or more etched areas 86 may be formed on the surface of the inner rod 82. In some cases, the etched areas 86 may be formed by etching away the electrically insulating material. In some instances, while named etched areas 86, the etched areas 86 may instead be formed by masking off these areas when coating the inner rod 82 with the electrically insulating material. These are just examples. In some cases, the inner rod 82 includes an etched area 88 at or near a proximal end 90 of the inner rod 82 so that electrical connection may be made to the inner rod 82. In some instances, each of the etched areas 86 may be uniform in size and uniformly spaced apart. In some cases, the etched areas 86 may vary in length or width, and may vary in relative spacing in order to provide improved resolution, for example.

The outer sheath 84 includes a detection region 92 that is defined in part by a front seal 94 and a rear seal 96. In some cases, the front seal 94 and/or the rear seal 96 may be O-rings, but this is not required in all cases. An internally exposed coil 98 is disposed relative to the detection region 92. The outer sheath 84 also includes an externally exposed coil 100 that is electrically coupled to the internally exposed coil 98 via conductors 102. It will be appreciated that the externally exposed coil 100 may provide a conductive path through the patient to an externally located electrode patch. In some instances, the externally exposed coil 100 may be used to couple to an external coil that inductively (for example) couples with the externally exposed coil 100 such that current flowing through the externally exposed coil 100 may cause a current to flow in the externally coupled coil. In some cases, a current may be applied to the inner rod 82, which can be measured to determine the exposed area of the one or more etched areas 86. In some cases, the internally exposed coil 98 and/or the externally exposed coil 100 may be coils that serve mechanical functions within the medical delivery device 80.

Figure 9:
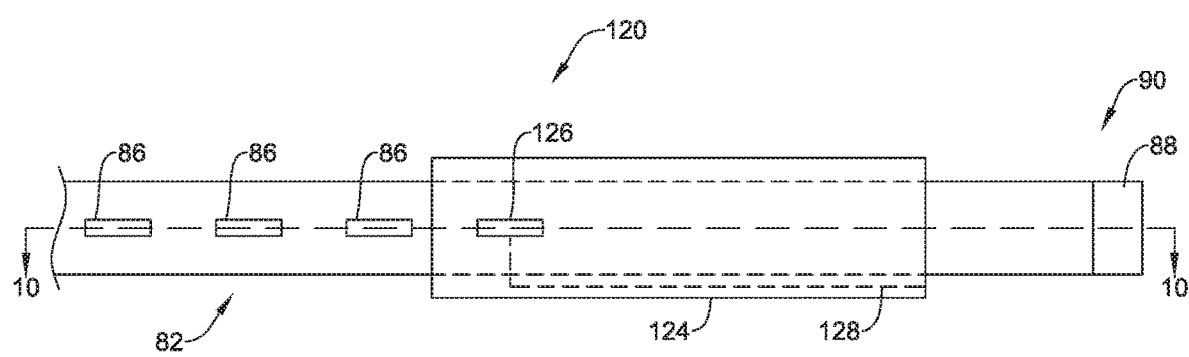
FIG. 9 is a partial view of an example medical device delivery system.

FIG. 9 shows a portion of an example medical delivery device 120. It will be appreciated that some features and elements of the medical delivery device 120 may not be illustrated for clarity purposes. The medical delivery device 120 includes an inner rod 82 that is slidingly disposed within an outer sheath 124. In some cases, the inner rod 82 may be considered as representing the actuation rod 40 and the outer sheath 124 may be considered as representing a portion of the inner catheter 14 discussed with respect to previous drawings. In some cases, the outer sheath 124 includes an electrically insulating layer. In some instances, the outer sheath 124 may represent or be a portion of the coil member 38 extending through the lumen 25.

As noted with respect to FIG. 8, the inner rod 82 may be formed of an electrically conductive material and may be covered with an electrically insulating material. In some cases, the electrically insulating material may be a polymer such as Parylene or expanded polytetrafluoroethyene (better known as Teflon). One or more etched areas 86 may be formed on the surface of the inner rod 82. In some cases, the etched areas 86 may be formed by etching away the electrically insulating material. In some instances, while named etched areas 86, the etched areas 86 may instead be formed by masking off these areas when coating the inner rod 82 with the electrically insulating material. These are just examples. In some cases, the inner rod 82 includes an etched area 88 at or near a proximal end 90 of the inner rod 82 so that electrical connection may be made to the inner rod 82. In some cases, the etched area 88 is exposed in another manner, as long as the etched area 88 is electrically active.

Figure 9A:
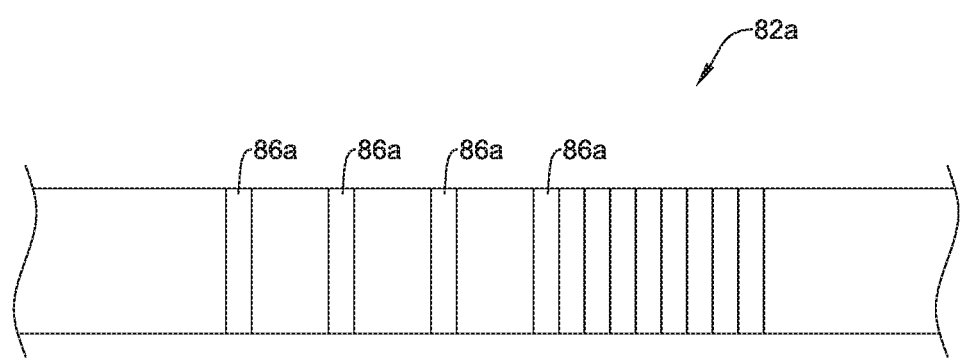
FIG. 9A and FIG. 9B are partial views of a portion of the example medical device delivery system of FIG. 9.
Figure 9B:
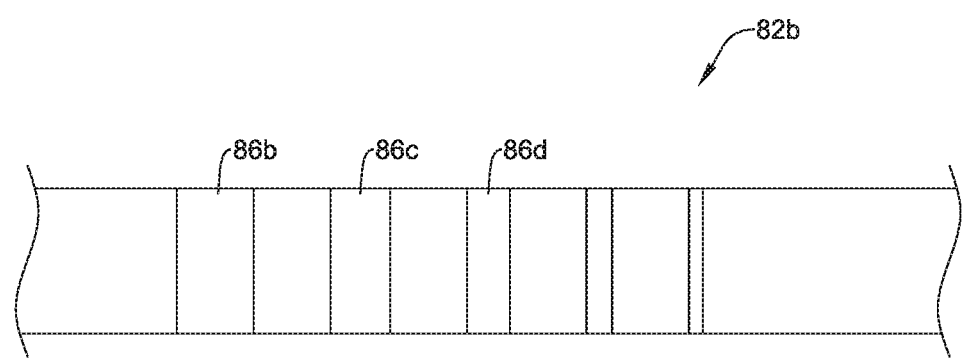

In some instances, each of the etched areas 86 may be uniform in size and uniformly spaced apart. In some cases, the etched areas 86 may vary in length or width, and may vary in relative spacing in order to provide improved resolution, for example. This can be seen in FIG. 9A and FIG. 9B. FIG. 9A shows an inner rod 82a that includes a number of etched areas 86a that each extend at least partially radially around the inner rod 82a. While each of the etched areas 86a are roughly the same size, it can be seen that the relative spacing between adjacent etched areas 86a varies over the length of the inner rod 82a. FIG. 9B shows an inner rod 82b that includes a number of etched areas that each extend at least partially radially around the inner rod 82b. While the relative spacing between adjacent etched areas remains roughly constant, the size of each etched area varies. For example, an etched area 86b is larger than an etched area 86c, which in turn is larger than an etched area 86d, and so on.

Figure 10:
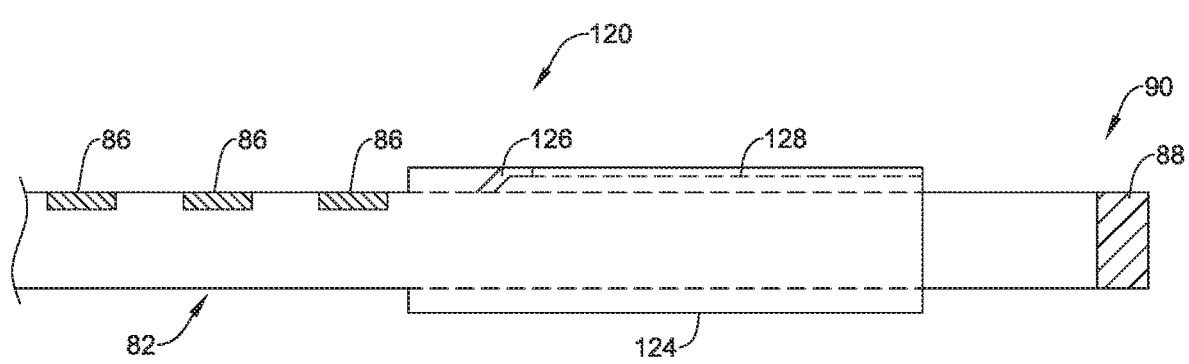
FIG. 10 is a cross-sectional view of the example medical device delivery system of FIG. 9.

Returning to FIG. 9, the outer sheath 124 includes a resilient switch 126 that may be configured to make contact with the etched areas 86 on the inner rod 82 (or 82a or 82b, for example). As best seen in FIG. 10, which is a cross-sectional view along line 10-10 of FIG. 9, the resilient switch 126 may be configured to make electrical contact with the etched areas 86 as the inner rod 82 translates relative to the resilient switch 126. The resilient switch 126 includes one or more electrical connections 128 that are electrically coupled with the resilient switch 126 and extend towards the handle 17 (FIG. 1).

Figure 11:
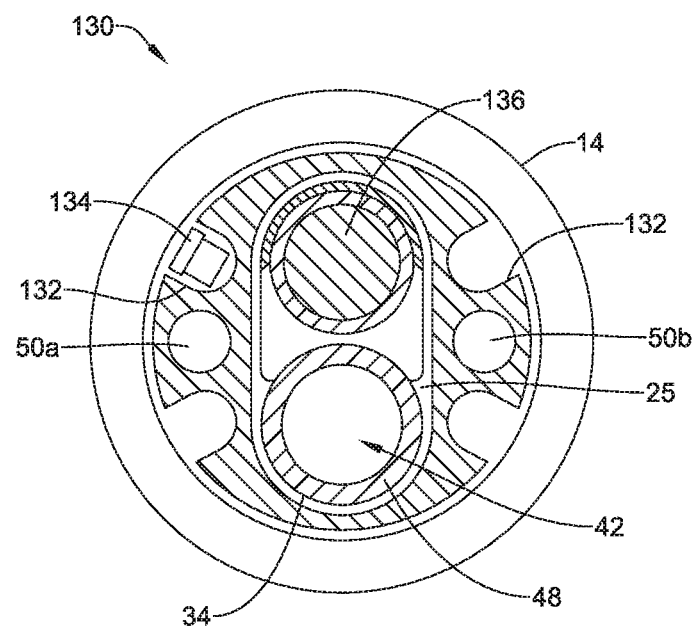
FIG. 11 is a partial view of an example medical device delivery system.
Figure 12:
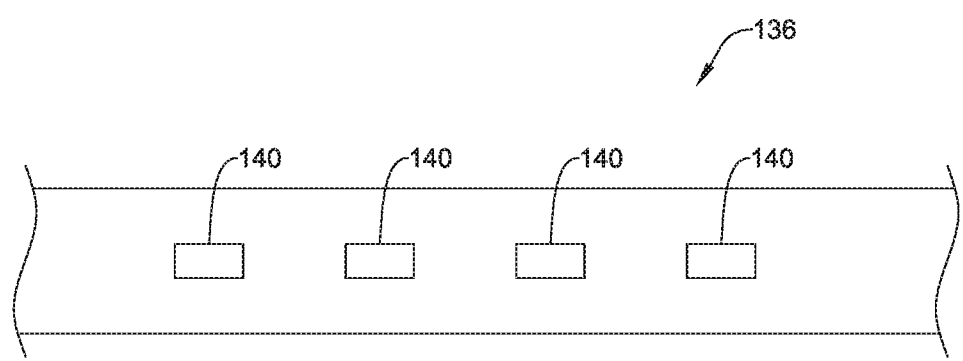
FIG. 12 is a partial view of a portion of the example medical device delivery system.
Figure 13:
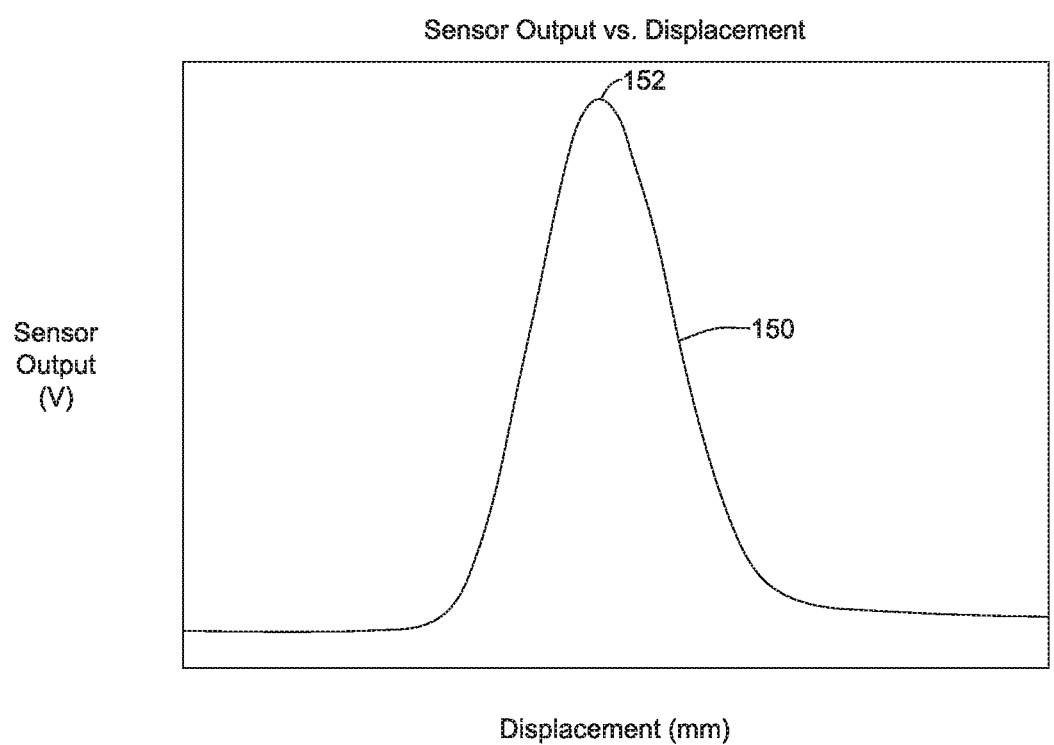
FIG. 13 is a graphical representation of operation of the example medical device delivery system of FIG. 10.

In some cases, a magnetic switch may be used. FIG. 11 is a cross-sectional view of a portion of an example medical delivery device 130 which is similar to the cross-sectional view shown in FIG. 6, although the inner shaft includes several longitudinally extending slots 132 formed on an outer surface of the inner shaft. In some cases, these longitudinally extending slots 132 may be used to convey wires from a position sensor as described in FIGS. 8 through 11. In some cases, as illustrated, a magnetic switch 134 may be disposed in one of the longitudinally extending slots 132. The magnetic switch 134 may be sensitive to ferromagnetic segments 140, which as shown in FIG. 12 are spaced, equally or variably, along the inner rod 136. As can be seen in FIG. 13, which provides a plot of sensor output (in volts) versus displacement (in millimeters), a magnetic switch can provide an easily seen indication of position, as a good signal can be obtained. The plot includes a line 150 having a peak 150 that provides a strong signal. In some cases, a reed switch may be used. In some cases, a Hall effect sensor may be used.

The materials that can be used for the various components of the medical devices and/or system 10 disclosed herein may include those commonly associated with medical devices. However, this is not intended to limit the devices and methods described herein, as the discussion may be applied to other components of the medical devices and/or systems 10 disclosed herein including the various shafts, liners, components described relative thereto.

The medical device 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), high density polyethylene (HDPE), polyester, Marlex high-density polyethylene, Marlex low-density polyethylene, linear low density polyethylene (for example REXELL®), ultra-high molecular weight (UHMW) polyethylene, polypropylene, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP).

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the medical device 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device 10 to achieve the same result.

In some embodiments, a degree of Magnetic Resonance Imaging (MM) compatibility is imparted into the medical device 10. For example, the medical device 10 may include a material that does not substantially distort the image and create substantial artifacts (e.g., gaps in the image). Certain ferromagnetic materials, for example, may not be suitable because they may create artifacts in an MRI image. The medical device 10 may also be made from a material that the MM machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A delivery system for an implantable medical device, comprising:
    an outer shaft defining an outer shaft lumen;
    an inner shaft translatable within the outer shaft lumen;
    an internally exposed coil disposed within the inner shaft and electrically coupled to an externally exposed coil that can be used to conductively transmit a current flowing through the internally exposed coil;
    the inner shaft defining a lumen extending through the inner shaft;
    an actuation mechanism extending through the lumen, the actuation mechanism including a coupler, a force translation rod that extends proximally from the coupler and a plurality of push pull rods that extend distally from the coupler and that releasably couple to the implantable medical device;
    the force translation rod formed of an electrically conducting material with an electrically insulating outer layer, with one or more etched areas extending through the electrically insulating outer layer, wherein when the force translation rod moves relative to the inner shaft, and thus the one or more etched areas move relative to the internally exposed coil, an impedance varies in accordance with a relative position therebetween.

2. The delivery system of claim 1, further comprising a detection region formed in the inner shaft and the internally exposed coil is disposed relative to the detection region.

3. The delivery system of claim 2, further comprising a front seal disposed at a front edge of the detection region and a rear seal disposed at a rear edge of the detection region.

4. The delivery system of claim 3, wherein the front seal and/or the back seal comprise an O-ring.

5. The delivery system of claim 1, wherein the force translation rod comprises an etched or otherwise exposed proximal end so that electrical contact can be made with the force translation rod.

6. The delivery system of claim 1, wherein the electrically insulating outer layer on the force translation rod comprises a polymer.

7. The delivery system of claim 1, wherein the electrically insulating outer layer on the force translation rod comprises Parylene or expanded polytetrafluoroethylene.

8. The delivery system of claim 1, wherein each of the one or more etched areas are electrically conductive.

9. The delivery system of claim 1, wherein each of the one or more etched areas are located a known distance from the coupler.

* * * * *